United States Patent
Dimitrov

(10) Patent No.: US 10,139,361 B2
(45) Date of Patent: Nov. 27, 2018

(54) PROTEOLYSIS DETECTION

(75) Inventor: Krassen Dimitrov, Indooroopilly (AU)

(73) Assignee: The University of Queensland, Queensland (AU)

(*) Notice: Subject to any disclaimer, the term of this patent is extended or adjusted under 35 U.S.C. 154(b) by 0 days.

(21) Appl. No.: 13/978,702

(22) PCT Filed: Dec. 22, 2011

(86) PCT No.: PCT/AU2011/001672
§ 371 (c)(1),
(2), (4) Date: Oct. 18, 2013

(87) PCT Pub. No.: WO2012/092646
PCT Pub. Date: Jul. 12, 2012

(65) Prior Publication Data
US 2014/0038218 A1    Feb. 6, 2014

(30) Foreign Application Priority Data
Jan. 7, 2011    (AU) ................... 2011900035

(51) Int. Cl.
*G01N 27/327* (2006.01)
*G01N 33/49* (2006.01)
*G01N 33/86* (2006.01)

(52) U.S. Cl.
CPC ..... *G01N 27/3275* (2013.01); *G01N 33/4905* (2013.01); *G01N 33/86* (2013.01)

(58) Field of Classification Search
CPC .... G01N 33/86; G01N 27/26; G01N 27/3275; G01N 33/4905
See application file for complete search history.

(56) References Cited

U.S. PATENT DOCUMENTS

| | | |
|---|---|---|
| 4,699,876 A | 10/1987 | Libeskind |
| 5,385,846 A | 1/1995 | Kuhn et al. |
| 5,909,114 A | 6/1999 | Uchiyama et al. |
| 6,046,051 A | 4/2000 | Jina |
| 9,453,833 B2 | 9/2016 | Dimitrov |
| 2005/0186635 A1 | 8/2005 | Bamdad et al. |
| 2008/0096495 A1 | 4/2008 | Shen |
| 2009/0060999 A1 | 3/2009 | Lyngstadaas et al. |
| 2011/0250616 A1 | 10/2011 | Bamdad et al. |

FOREIGN PATENT DOCUMENTS

| | | |
|---|---|---|
| AU | 2005203615 | 9/2005 |
| EP | 1482296 | 12/2004 |
| JP | 60-176589 A | 9/1985 |
| JP | 2000-35427 A | 2/2000 |
| JP | 2005-83928 A | 3/2005 |
| JP | 2009-244013 A | 10/2009 |
| JP | 2009-264920 A | 11/2009 |
| JP | 2010-2401 A | 1/2010 |
| KR | 10-0945571 B1 | 3/2010 |
| WO | WO 2009/064983 A1 | 5/2009 |
| WO | 2012/092646 A1 | 7/2012 |
| WO | 2013/039362 A2 | 3/2013 |

OTHER PUBLICATIONS

Lee et al. "The Role of the Coagulation Cascade in Brain Edema Formation after Intracerebral Hemorrhage" (1996) Acta Neurochir, vol. 138: 396-401.*
Adjemian et al. "Cleavage-Sensing Redox Peptide Monolayers for the Rapid Measurement of the Proteolytic Activity of Trypsin and alpha-Thrombin" (2010) Langmuir, vol. 26, No. 12: 0347-10356.*
Bas et al., "Rapid Method for Quantitative Determination of Proteolytic Activity with Cyclic Voltammetry," *Electroanalysis* 22(3):265-267, 2010.
Extended Search Report for EP 11854784.3 dated Apr. 7, 2014.
International Search Report and Written Opinion, dated Apr. 17, 2015, for corresponding International Application No. PCT/US2014/073030, 16 pages.
Ryan et al., "Influence of a Natural and a Synthetic Inhibitor of Factor XIIIa on Fibrin Clot Rheology," *Biophysical Journal* 77: 2827-2836, Nov. 1999.
Official Action from Patent Office of Australia, dated Jul. 25, 2016, for Patent Application No. 2011354498, 10 pages.
Kumar et al., "Smart polymers: Physical forms and bioengineering applications," *Prog. Polym. Sci.* 32: 1205-1237, 2007.
Stoller et al., "Best practice methods for determining an electrode material's performance for ultracapacitors," *Energy Environ. Sci.* 3: 1294-1301, 2010.
Gracia et al., "Polymers with redox properties: materials for batteries, biosensors and more," *Polym. Chem.* 4: 2206-2214, 2013.

* cited by examiner

*Primary Examiner* — Teresa E Knight
(74) *Attorney, Agent, or Firm* — Seed IP Law Group LLP

(57) ABSTRACT

Disclosed are electrochemical methods, apparatus, systems and kits for the detection or monitoring of proteolysis of proteinaceous matrices such as fibrin clots. The methods, apparatus, systems and kits generally include the use of voltammetric techniques to measure the changes in current that result from diffusion of an electroactive species towards an electrode on proteolysis of a proteinaceous matrix.

12 Claims, 11 Drawing Sheets

A.

B.

| Gold chip2, E6 (given by SR on 17 Sep 10) | Amperometric response |
|---|---|
| Before clotting | 6.5 e-6 A |
| After clotting and incubation | 2.1 e-6 A |
| After plasmin addition and 7 min incubation | 3.4 e-6 A |

C.

D.

A.

B.

C.

D.

A.

B.

C.

D.

E.

F.

G.

PROTEOLYSIS DETECTION

TECHNICAL FIELD

The present invention relates to electrochemical methods, apparatus, systems and kits for the detection or monitoring of proteolysis of proteinaceous matrices such as fibrin clots.

BACKGROUND

Protein matrices are important for tissue function, tissue regeneration, wound healing, and hemostasis. For example many eukaryotic cells are enveloped by an extracellular matrix of proteins that provide structural support, cell and tissue identity, and autocrine, paracrine and juxtacrine properties for the cell and the matrix is thus required for normal tissue functions. In wound healing a cascade of molecular and cellular events initially leads to hemostasis, the prevention of blood loss. Fibrin plays a crucial role in hemostasis and wound healing as it forms a crosslinked proteinaceous matrix (clot) by means of a complex cascade of reactions with the final steps being the conversion of monomeric fibrinogen by thrombin, to form a crosslinked fibrin polymer, which is often referred to as a clot.

In addition to its role in hemostasis, fibrin formation is common in a number of pathological and inflammatory conditions. For example, abnormal fibrin deposition (thrombosis) is associated with atherosclerosis, rheumatoid arthritis, glomerulonephritis, systemic lupus erythematosus, myocardial infarcts, stroke, pulmonary embolism, deep vein thrombosis, autoimmune neuropathies, granulomatous disease, parasitic infections and allograft rejection. There is also evidence that thrombosis plays a role in neurodegenerative disease.

Protein matrices such as extracellular matrix and fibrin clots are typically dynamic, that is the matrix can be formed and degraded as part of pathological processes or normal physiological processes. Indeed, hemostasis can be viewed as the maintenance of equilibrium between the formation of fibrin clots (coagulation) and the proteolytic degradation of those clots (fibrinolysis) by factors including plasmin.

Methods for detection or monitoring of the formation of protein matrices such as blood clots (thrombi) include for example methods of determining blood coagulation e.g., prothrombin time, thrombin clotting time or the Clauss method for fibrinogen testing, and there are commercial devices that can perform such coagulation testing in portable, point-of-care formats. However, tests for detection or monitoring of proteolysis are typically limited to complex methods in specialized laboratories, such as, for example thromboelastometry (TEM), and are not applicable to point of care or field diagnostics. Other methods use colorimetric or fluorescent detection methodologies and are, too, expensive, complex and are negatively affected by the color or turbidity of a sample.

There exists a need for methods, apparatus and systems for detection and/or monitoring of proteolysis of protein matrices. In particular, detection of fibrinolytic activity in the blood can be a valuable medical diagnostics tool.

SUMMARY

The invention is predicated in part on the finding that electrochemical current generated by the oxidation or reduction of an electrochemically active compound is dependent on the rate of diffusion of that compound within a protein matrix, such as fibrin clot. This finding has been reduced to practice in methods, systems and kits that take advantage of changes in electrochemical current to detect or monitor proteolysis of a proteinaceous matrix by a protease-containing sample under test and/or to qualitatively or quantitatively determine protease activity in a test sample.

In a first aspect there is provided a method for detecting or monitoring proteolysis of a proteinaceous matrix comprising:
  providing a working electrode, a counter electrode, a proteinaceous matrix and an electrolytic solution comprising an electroactive species wherein the proteinaceous matrix is in contact with at least a portion of at least one electrode;
  applying a potential thereby generating an electrochemical current through said working electrode;
  measuring said current at a plurality of times; and
  comparing at least two of the measurements wherein a difference between the measurements is indicative of degradation of said proteinaceous matrix.

In a second aspect there is provided a method for screening a sample obtained from a subject for proteolytic activity, the method comprising;
  providing a working electrode, a counter electrode, a proteinaceous matrix and an electrolytic solution comprising an electroactive species wherein the proteinaceous matrix is in contact with at least a portion of at least one electrode;
  contacting the proteinaceous matrix with a sample putatively having proteolytic activity;
  applying a potential to said working electrode thereby generating an electrochemical current through said working electrode;
  measuring said current at a plurality of times; and
  comparing at least two of the measurements wherein a difference between the measurements is indicative of proteolytic activity.

The method may further comprise altering the potential over time.

The counter electrode may comprise a reference electrode and an auxiliary electrode.

The potential may be altered linearly, cyclically or in steps.

The measurements may be qualitative or quantitative.

The sample may be a biological sample such as a bodily fluid, excretion or secretion. For example the sample may be selected from selected from the group comprising blood, blood plasma or blood serum.

The proteinaceous matrix may be selected from a fibrin clot, blood clot, platelet rich plasma (PRP) clot, or collagen matrix. The proteinaceous matrix may be naked (e.g., unsupported) or contained or otherwise associated with a porous support (e.g., filter paper, sintered glass, poly(vinylidene fluoride) membrane or gel).

Suitably, the method comprises correlating the difference between the measurements to thereby qualitatively or quantitatively determine the amount of proteolytic activity in the sample. In some embodiments, the proteinaceous matrix is a fibrin clot, PRP clot or blood clot, and the proteolytic activity in the sample is provided at least in part by plasmin. In other embodiments the proteinaceous matrix is collagen, and the proteolytic activity in the sample is provided at least in part by one or more collagenases (e.g., matrix metalloproteases (MMPs) such as MMP-1, MMP-8, MMP-13, MMP-18 etc.).

In a third aspect there is provided an electrode comprising a proteinaceous matrix in contact with at least an electrically conductive material.

The electrically conductive material may be gold, silver, platinum, ruthenium dioxide, palladium, conductive carbon, platinum or ITO (indium tin oxide), as well as other non-corroding materials known to those skilled in the art, or combinations thereof.

In a fourth aspect there is provided a porous support comprising a proteinaceous matrix (e.g., for use in the methods and systems of the present invention). The support may be a sorbent, filter paper or other filters, sintered glass, poly(vinylidene fluoride) membrane or gel.

In a fifth aspect there is provided a system for voltammetric detection or monitoring of proteolysis of a proteinaceous matrix, the system comprising:
 a working electrode;
 a counter electrode to which a potential is applied;
 a current registration unit arranged to register current passed through the working electrode;
 a control unit arranged to control said potential and said working electrode, said control unit further arranged to read current values from said current registration unit at predetermined times;
 a data storage unit for storing said current values; and
 a processing unit arranged to analyze the stored current values using a predetermined mathematical model and to output a result from the analysis.

The system may further comprise a proteinaceous matrix in contact with at least a portion of the counter electrode or working electrode.

The counter electrode may comprise a reference electrode and an auxiliary electrode.

The working electrode, the counter electrode, the current registration unit and the control unit may be integrated as one device arranged to output the current values to an external data storage unit and processing unit.

The working electrode, the counter electrode, the current registration unit, the control unit, the data storage unit and the processing unit may be integrated as one device arranged to output the result from the analysis.

In a sixth aspect there is provided a kit for detecting or monitoring degradation of a proteinaceous matrix, the kit comprising at least one proteinaceous matrix. The kit may further comprise at least one or any combination of the following:
 (1) an electrode in contact with the proteinaceous matrix;
 (2) a porous support comprising the proteinaceous matrix, wherein the support is selected for example from a sorbent, filter paper or other filters, sintered glass, poly(vinylidene fluoride) membrane or gel;
 (3) at least one electrolytic solution, electroactive species, salts and/or control samples with known levels of proteolytic activity;
 (4) components for generating the proteinaceous matrix for example a protein and a crosslinking agent, or for example fibrinogen and thrombin.

In any one of the preceding aspects the proteinaceous matrix may comprise covalently on non-covalently crosslinked proteins. The matrix may further comprise cells, lipids, carbohydrates, sugars or salts. The protein matrix may comprise or consist essentially of a single protein type or may comprise multiple protein types.

BRIEF DESCRIPTION OF THE DRAWINGS

Embodiments of the invention are described and exemplified herein, by way of non-limiting example only, with reference to the following figures.

DEFINITIONS

Figure 1:
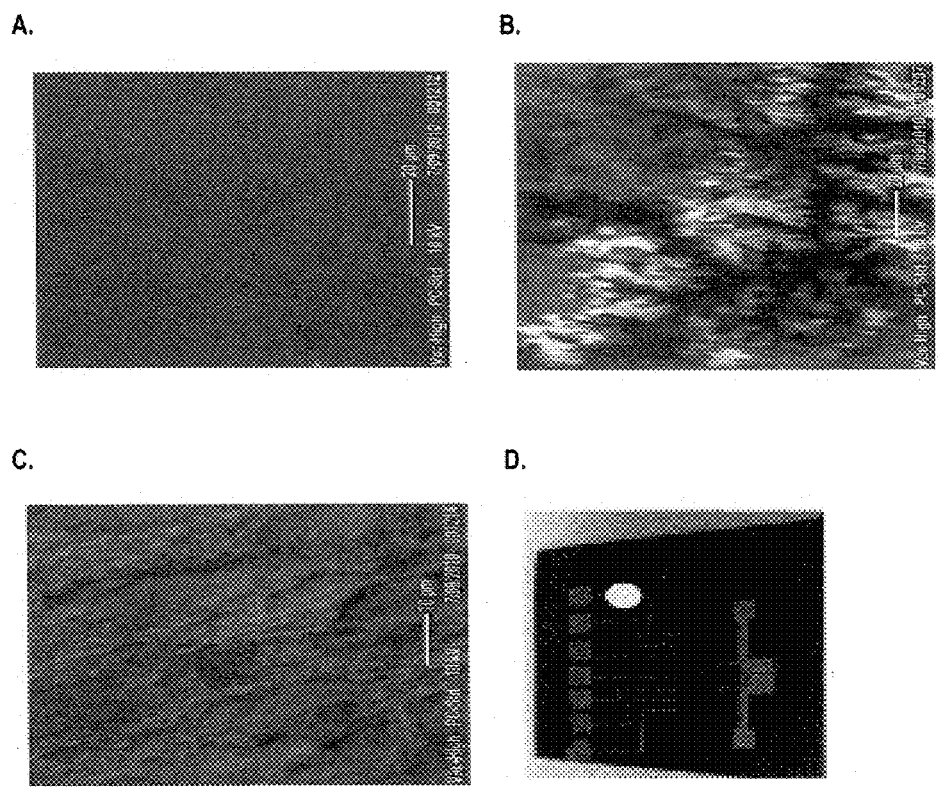
FIG. 1 shows: (A) an electron micrograph of the surface of a gold electrode, scale bar is 20 µm; (B) an electron micrograph of the surface a gold electrode with a 2% fibrin clot in 1×PBS (phosphate buffered saline: 137 mM NaCl, 2.7 mM KCl, 10 mM sodium phosphate dibasic, 2 mM potassium phosphate monobasic and a pH of 7.4) on the electrode surface, scale bar is 20 µm; (C) an electron micrograph of the surface of a gold electrode with a 2% fibrin clot in 0.1×PBS (13.7 mM NaCl, 0.27 mM KCl, 1 mM sodium phosphate dibasic, 0.2 mM potassium phosphate monobasic and a pH of 7.4) on the electrode surface, scale bar is 10 µm; (D) Image of a sensor chip with multiple electrodes. Shown is the placement of a filter containing human fibrin clot.

Certain terms are used herein which shall have the meanings set forth as follows.

As used in this application, the singular form "a", "an" and "the" include plural references unless the context clearly dictates otherwise. For example, the term "matrix" or "proteinaceous matrix" also includes a plurality of matrices or proteinaceous matrices respectively. Unless the context requires otherwise or specifically stated to the contrary, integers, steps, or elements of the invention recited herein as singular integers, steps or elements clearly encompass both singular and plural forms of the recited integers, steps or elements.

By "about" is meant a measurement, quantity, level, activity, value, number, frequency, percentage, dimension, size, amount, weight or length that varies by as much as 10, 9, 8, 7, 6, 5, 4, 3, 2 or 1% to a reference measurement, quantity, level, activity, value, number, frequency, percentage, dimension, size, amount, weight or length.

The terms "biological sample" as used herein refers to a sample that may be extracted, untreated, treated, diluted or concentrated from a subject. The biological sample may include a biological fluid such as whole blood, serum, plasma, saliva, urine, sweat, ascitic fluid, peritoneal fluid, synovial fluid, amniotic fluid, cerebrospinal fluid, tissue biopsy, lymph fluid, interstitial fluid, and the like. In certain embodiments, the biological sample comprises blood.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The term "electroactive species" as used herein is defined as a substance that may be oxidized or reduced and that may transfer one or more electrons. An electroactive species is a reagent in an electrochemical analysis and provides for the indirect measurement of the proteolysis of a proteinaceous matrix. Generally, "electroactive species" reduce or oxidize in aqueous solutions at potentials below those required for electrolysis of water, thereby being active in conditions where water electrolysis does not generate significant Faradic currents.

The term "redox pair" as used herein refers to two conjugate species of a chemical substance having different oxidation numbers. Reduction of the species having the higher oxidation number produces the species having the lower oxidation number. Alternatively, oxidation of the species having the lower oxidation number produces the species having the higher oxidation number.

The term "proteolysis" as used herein refers to the breakdown of proteins into smaller polypeptides and the resulting degradation of protein fibers. The breakdown may occur by cleavage of peptide bonds due to enzymatic or chemical mechanisms. The breakdown may occur by cleavage of crosslinks between homologous or heterologous proteins. Proteolysis may result in breakdown of the protein into individual amino acids.

The term "electrode" as used herein means an electric conductor through which a potential can be measured. An electrode can also be a collector and/or emitter of an electric current. Suitably, an electrode is a solid and comprises a conducting metal. Preferable conducting metals include alloys such as indium tin oxide, conductive carbon, or noble metals such as gold, silver, palladium or platinum. An electrode can also be a wire or microwire, or the term "electrode" can describe a collection of wires or microwires.

DETAILED DESCRIPTION

It is to be understood at the outset, that the figures and examples provided herein are to exemplify and not to limit the invention and its various embodiments.

Methods, apparatus, systems and kits are provided for the detection or monitoring of the proteolysis of a proteinaceous matrix, which typically include the use of voltammetric techniques to measure the changes in current due to diffusion of an electroactive species towards an electrode on proteolysis of a proteinaceous matrix.

Proteinaceous Matrices

The proteinaceous matrices of the invention may be any protein matrix known in the art. For example the protein matrix may exist naturally such as extracellular matrix or may be formed naturally, such as by coagulation of blood or the action of thrombin on fibrinogen. In some embodiments, a synthetic proteinaceous matrix is formed in vitro. In some embodiments, the proteinaceous matrix is formed from one or more proteins that spontaneously form the matrix. Suitably, the proteinaceous matrix is formed by reaction of proteins with one or more polyanions and/or crosslinking agents. In some embodiments, the proteinaceous matrix is a fibrin matrix formed by contacting fibrinogen with thrombin. In other embodiments, the proteinaceous matrix is a collagen matrix (e.g., native or reconstituted aggregations of type I collagen molecules). In some embodiments, the proteinaceous matrix is a synthetic proteinaceous matrix formed in the absence of a cross-linking agent. In representative examples of this type, the proteinaceous matrix is a non-cross-linked proteinaceous matrix or has reduced (e.g., less than about 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1%) cross-linking relative a corresponding naturally occurring proteinaceous matrix. In some of these examples, the synthetic proteinaceous matrix suitably comprises a synthetic fibrin clot formed from fibrinogen and thrombin but in the absence of a cross-linking agent (e.g., Factor XIII). In specific embodiments of this type, the synthetic fibrin clot is formed in the presence of higher levels or concentrations of fibrinogen (e.g. 1.5%, 2% 4%, 5%, 10%, 15% wt.), relative to native blood (0.3-0.4% wt).

In some embodiments, the proteinaceous matrix lacks a proteolysis inhibitor or comprises a reduced amount, level or concentration (e.g., less than about 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1%) of proteolysis inhibitor as compared to a corresponding naturally occurring proteinaceous matrix. In illustrative examples of this type, the proteinaceous matrix comprises a fibrin clot but lacks a fibrinolysis inhibitor (e.g., α-antiplasmin).

Biological fluids may be reacted with certain agents to form protein matrices. The biological fluids may be blood, plasma, serum, urine, cerebrospinal fluid, tears, saliva, milk, mucus, sputum, peritoneal cavity fluid.

Alternatively, such fluids may be synthetically prepared compositions, e.g., tissue culture medium, tissue culture medium containing proteins, synthetic polymers, polymers with functional groups found on proteins such as amines, sulfhydryl, carboxyls or hydroxyls, amine-terminated polyethylene glycol, amine-terminated polyethers, or mixtures of thereof. Non-limiting examples of proteins suitable for use in preparing protein matrices include fibrinogen, fibrin, collagen, fibronectin, and laminin. Methods for making such matrices are well known in the art.

In some embodiments, the proteinaceous matrix comprises non-protein components such as cells, lipids, carbohydrates, sugars, salts and the like.

The proteinaceous matrix generally substantially inhibits diffusion of an electroactive species. From a physical perspective, the protein fibers in the proteinaceous matrix generally interact to form a porous substance with very high dynamic viscosity (e.g., >2 Pa·s). From Einstein-Stokes equation, the diffusion constant, D, is given by $$D = \frac{k_B T}{6\pi \eta r}$$

where:
$k_B$ is Boltzmann's constant,
T is the absolute temperature,
$\eta$ is the dynamic viscosity
r is the molecular or ionic radius of the electroactive species.

When the protein fibers in the matrix are broken down proteolytically, the porosity of the matrix increases, the viscosity decreases, and the diffusion constant increases.

The proteinaceous matrix may be subjected to a mechanical or physical treatment. The mechanical treatment may include compression or extrusion.

In some embodiments, the proteinaceous matrix comprises an electroactive species that is capable of being oxidized or reduced to form a charged species. Non-limiting examples of electroactive species include ferricyanide, ferrocyanide, decamethylferrocene (DMFc), 1,1'-dimethylferrocene (DiMFc), 7,7,8,8-tetracyanoquinodimethane (TCNQ) and ferrocene carboxylic acid.

In specific embodiments, the proteinaceous matrix is subjected to dehydration. In these embodiments, the proteinaceous matrix is suitably rehydrated when contacted with a sample (e.g., a biological sample) under test. The dehydration can be performed in an oxygen-containing atmosphere (e.g., air), or in an inert atmosphere, such as a nitrogen atmosphere. Desirably, the dehydration is selected from lyophilization (i.e., freeze drying), heat dehydration (e.g., at ambient temperature), osmosis, filtration and centrifugation. After dehydration, the proteinaceous matrix desirably has a low moisture content, for example a moisture content of less than about 7.5%, less than about 2%, less than about 1%.

In some embodiments, the proteinaceous matrix is a fibrin clot, PRP clot or blood clot, and the proteolytic activity in the sample is provided at least in part by plasmin. In other embodiments the proteinaceous matrix is collagen, and the proteolytic activity in the sample is provided at least in part by one or more collagenases (e.g., matrix metalloproteases (MMPs) such as MMP-1, MMP-8, MMP-13, MMP-18 etc.).

The proteinaceous matrix may be attached to or formed on an electrode (e.g., working electrode) using conventional methods known to persons of skill in the art, such as for example by screen printing, or ink-jet printing, or robotic pipetting.

Supports

The invention also provides a support comprising a proteinaceous matrix. The support may be a porous support. It will be understood that the pores of the support may be substantially interconnecting and/or extend through the volume of the support. In other embodiments, the pores may be substantially unconnected and extend through the volume of the support. Suitably, at least a portion of the proteinaceous matrix is contained in the pores. Illustrative examples of porous supports include papers such as sorbents, filter paper, filter membranes, sintered glass, poly(vinylidene fluoride) membranes, and gels. The proteinaceous matrix-containing solid supports of the present invention are especially advantageous as they can be manufactured in large quantities with greater consistency in pore size and pore volume of one and preferably both of the solid support and the proteinaceous matrix, which suitably improves inter or intra-assay reliability and consistency.

In specific embodiments, the solid supports are porous. Illustrative porous solid supports have a structure comprising pores of a diameter that is substantially greater than the pore diameter of the proteinaceous matrix. For example, the pore at least about 5.0 µm, at least about 10.0 µm, and is suitably 20 µm or more as larger pores are less restrictive to diffusion of an electroactive species.

In some embodiments, the solid supports further comprise an electroactive species that is capable of being oxidized or reduced to form a charged species (e.g., ferricyanide, ferrocyanide, decamethylferrocene (DMFc), 1,1'-dimethylferrocene (DiMFc), 7,7,8,8-tetracyanoquinodimethane (TCNQ), ferrocene carboxylic acid, etc).

The proteinaceous matrix-containing solid supports may be subjected to a mechanical or physical treatment. The mechanical treatment may include compression or extrusion. Representative physical treatments include dehydration (e.g., lyophilization, heat dehydration etc.) and radiation (e.g., light). The mechanical or physical treatment is suitably carried out under sterile conditions.

In specific embodiments, the solid supports are subjected to dehydration, thereby resulting in solid supports that are in substantially dehydrated form. In these embodiments, the solid supports are suitably rehydrated when contacted with a sample (e.g., a biological sample) under test. The dehydration can be performed in an oxygen-containing atmosphere (e.g., air), or in an inert atmosphere, such as a nitrogen atmosphere. Suitably, the dehydration is selected from lyophilization (i.e., freeze drying), heat dehydration (e.g., at ambient temperature), osmosis, filtration and centrifugation. After dehydration, the solid supports desirably have a low moisture content, for example a moisture content of less than about 7.5%, less than about 2%, less than about 1%, or less than about 0.5%. Dehydration of the solid supports has several advantages including reducing degradation and improving shelf life of the proteinaceous matrix. It also permits better or more efficient contact of a putatively protease-containing sample with the proteinaceous via capillary flow or 'wicking' of the sample therethrough.

In some embodiments, the solid support is attached to an electrode (e.g., a working electrode) using conventional methods known to persons of skill in the art such as adhesion with adhesives or thermal bonding.

Detection of Proteolysis

Proteolysis of protein matrices is detected by electrochemical methods including voltammetry. Voltammetry is a technique typically used to investigate mechanisms of electrolysis but as disclosed herein finds application in detecting or monitoring proteolysis of proteinaceous matrices, particularly in response to proteolysis. Various forms of voltammetry are useful in the practice of the present invention, including square wave voltammetry, staircase voltammetry, anodic or cathodic stripping voltammetry, adsorptive stripping voltammetry, alternating current voltammetry, rotated electrode voltammetry, normal or differential pulse voltammetry, chronoamperometry, chronocoulometry, or current versus time. In preferred embodiments, the voltammetry is potential step voltammetry, linear sweep voltammetry or cyclic voltammetry. Either peak current, or current at a specific time point, or steady state current, or total charge transferred can be used as a measurement variable.

In each of these types of voltammetry, a voltage or series of voltages is applied to an electrode known as the working electrode and the corresponding current that flows is monitored. Typically the working electrode contacts an electroactive species, for example ferricyanide ($[Fe(CN)_6]^{3-}$) and a potential is applied to facilitate the transfer of charge to and from the electroactive species, thereby generating a current. A second electrode acts as the other half of an electrolytic cell. The role of the second electrode is to supply or subtract electrons to thereby maintain electroneutrality in the solution. If correct estimation of the potential at the working electrode relative to a known standard is required, the second electrode can be divided between two separate electrodes, the reference electrode and the auxiliary electrode. The reference electrode is a half-cell with a known reduction potential and which acts as reference in measuring and controlling the working electrodes potential and does not pass current. The auxiliary electrode passes the current needed to balance the current observed at the working electrode.

Thus the elements needed for an electrolysis measurement by voltammetry are at least two electrodes, a solvent, a background electrolyte and an electroactive species. The two electrodes are typically in contact with a solvent comprising the electrolyte and the electroactive species.

In some embodiments, a protein matrix is in contact with or present on at least a portion of a working electrode such that the mobility or diffusion of an electroactive species to the working electrode to transfer charge to or from that electrode is impaired or prevented. In other embodiments, a protein matrix is present on at least a portion of the second electrode and its ability to balance the charge added or removed by the working electrode is impaired or prevented. In further embodiments, a protein matrix is present on at least a portion of the working and the second electrodes. In these embodiments, the current measured on application of a potential is altered in comparison to the absence of a protein matrix. Accordingly, when the protein matrix is contacted with a proteolytic agent, for example by addition of such an agent or a sample putatively containing such an agent to the solvent or directly to the protein matrix, degradation of the protein matrix occurs. As the protein matrix is proteolyzed, the current measured on application of a potential also changes thereby allowing qualitative and/or quantitative detection and/or monitoring of the degradation of a protein matrix.

The background electrolyte is an electrochemically inert salt such as an aqueous solution of sodium chloride. In some embodiments, physiological fluid (0.9% sodium chloride) can be used as background electrolyte. The electroactive species typically present in low concentrations (e.g., in the order of 0.001, 0.002, 0.003, 0.004, 0.005, 0.006, 0.007, 0.008, 0.009, 0.01, 0.02, 0.03, 0.04, 0.05, 0.06, 0.07, 0.08, 0.09 or 0.1M). The electroactive species may be for example ferricyanide ($[Fe(CN)_6]^{3-}$).

The electroactive species is capable of being oxidized or reduced to form a charged species. That is the electroactive species forms a redox pair, for example when ferricyanide is the electroactive species a ferricyanide $[Fe(CN)_6]^{3-}$/ferrocyanide $[Fe(CN)_6]^{4-}$ redox pair. The electroactive species can be oxidized or reduced at the working electrode on application of a potential, thus causing electrochemical current in the working electrode. In some embodiments the electroactive species undergoes reversible oxidation or reduction. The electroactive species is preferably chemically stable.

Potential Step Voltammetry

In potential step voltammetry the applied voltage is switched or stepped from one value ($V_1$) to another ($V_2$). The resulting current is then measured as a function time. For example, using ferricyanide as the reactant the voltage range is typically set such that at $V_1$ the reduction of $[Fe(CN)_6]^{3-}$ is thermodynamically unfavorable. The second voltage ($V_2$) is typically selected so that any $[Fe(CN)_6]^{3-}$ close to the electrode surface is reduced to product $[Fe(CN)_6]^{4-}$.

In potential step voltammetry the current rises immediately after the switch (step) in voltage and then decreases over time. This occurs because before the voltage step the electrode is in contact with the electroactive species in the electrolytic solution has a constant composition however, once the voltage step occurs the electroactive species (e.g., $[Fe(CN)_6]^{3-}$) is converted to product (e.g., $[Fe(CN)_6]^{4-}$) and current flows. For the reaction to continue further electroactive species (e.g., $[Fe(CN)_6]^{3-}$) must approach the electrode. This typically occurs in solution by diffusion which is dependent on the concentration gradient of the electroactive species. So the supply of further electroactive species to the surface, and thus the flow of current, depends on the diffusional flux of the electroactive species.

As the electrolysis continues, electroactive species diffuses from greater distances from the electrode and thus the supply of electroactive species to the electrode surface drops, leading to a decrease in current.

The current can be calculated using the formula $$i = nFAk_{red}c^{bulk}\sqrt{\frac{D}{\pi t}} \propto t^{-1/2}$$

Where i is current, n is the number of moles of electrons transferred in the reaction, F is Faraday's constant (96,484 C mol$^{-1}$), A is the electrode area, $k_{red}$ is the rate constant for electron transfer, $c^{bulk}$ is the total concentration of the electroactive species, t is time and D is the diffusion coefficient of the electroactive species The current is related to the bulk concentration of the electroactive species which is the combined concentration of the reduced and oxidized species. Step voltammetry thus allows the estimation of the diffusion coefficients of the electroactive species. Consequently, in embodiments where the diffusion of an electroactive species is affected by the presence of a proteinaceous matrix estimations of the change in diffusion coefficients for example due to the proteolysis of a proteinaceous matrix can be used to detect of monitor the proteolysis of the proteinaceous matrix.

Linear Sweep Voltammetry

In linear sweep voltammetry (LSV), a fixed potential range is employed although the voltage is scanned from a lower limit ($V_1$) to an upper limit ($V_2$). The characteristics of the linear sweep voltammogram depend on a number of factors including the rate of the electron transfer reaction(s), the chemical reactivity of the electroactive species and the voltage scan rate.

In LSV as the voltage is swept to more reductive values a current begins to flow and eventually reaches a peak before dropping. At the electrode surface the rate of electron transfer is fast in comparison to the voltage sweep rate and at the electrode surface, an equilibrium is established substantially the same as that predicted by thermodynamics. As the voltage is initially swept from $V_1$ the equilibrium at the surface begins to alter and the current begins to flow. The current rises as the voltage is swept further from its initial value as the equilibrium is shifted and more electroactive species is reduced. A peak in the current occurs when the diffusion layer has grown sufficiently above the electrode so that the flux of electroactive species to the electrode is not fast enough to satisfy that required by the Nernst equation when the current begins to drop. The Nernst equation describes the relationship between the voltage of an electrochemical cell and the concentration of one of the components of the cell as follows.

$$E_{cell} = E^0_{cell} - (RT/nF) \ln Q$$

Where $E_{cell}$ is the cell potential after application of a potential to one electrode, $E^0_{cell}$ is the cell potential prior to applying the potential, R is the gas constant (8.31 (volt-coulomb)/(mol-K), T is the temperature (K), n is the number of moles of electrons exchanged in the electrochemical reaction (mol), F is Faraday's constant (96,484 C mol$^{-1}$) and Q is the reaction quotient (the equilibrium expression with initial concentrations rather than equilibrium concentrations The size of the diffusion layer above the electrode surface will be different depending upon the voltage scan rate used. In a slow voltage scan the diffusion layer will grow much further from the electrode in comparison to a fast scan. Consequently the flux to the electrode surface is considerably smaller at slow scan rates than it is at faster rates. As the current is proportional to the flux towards the electrode, the magnitude of the current will be lower at slow scan rates and higher at high rates.

The term "linear scan" is defined as a scan where the voltage is varied in a single "forward" direction at a fixed scan rate, such as from −0.7 V to +0.7 V against Ag/AgCl to provide a 1.4 V scan range A linear scan may be approximated by a series of incremental changes in potential. If the increments occur very close together in time, they correspond to a continuous linear scan. Thus, applying a change of potential approximating a linear change may be considered a linear scan.

During a linear scan the current at the working electrode is measured while the potential at the working electrode changes linearly with time at a constant rate. The scan range, such as from about −0.5 V to about +0.5 V from about −1.0 V to +1.0 V typically covers the reduced and oxidized states of a redox pair of the electroactive species so that a transition from one state (e.g., reduced) to the other (e.g., oxidized) occurs.

In some embodiments, the voltage is changed at a rate of at least about 10 mV/sec, or at least about 50 mV/sec, or at least about 100 mV/sec, or at least about 150 mV/sec, or at least about 200 mV/sec, or at least about 500 mV/sec, or at least about 1000 mV/sec, or at least about 2000 mV/sec.

Cyclic Voltammetry

Cyclic voltammetry (CV) is very similar to LSV although the voltage is swept or scanned in a cyclic manner (cyclic scan) between two values at a fixed rate, however now when the voltage reaches $V_2$ the scan is reversed and the voltage is swept back to $V_1$. The forward sweep produces an identical response to that seen in LSV experiment as the electroactive species is reduced. When the scan is reversed reduced electroactive species is oxidized and the current flow is reversed.

The term "cyclic scan" refers to a combination of a linear forward scan and a linear reverse scan where the scan range includes the oxidation and reduction peaks of a redox pair. For example, varying the potential in a cyclic manner from about −1.0 V to about +1.0 V and back to about −1.0 V is an example of a cyclic scan for the ferricyanide/ferrocyanide redox pair, where both the oxidation and reduction peaks are included in the scan range.

Methods

The present invention provides methods for detecting and/or monitoring the degradation of a proteinaceous matrix, particularly due to proteolysis. Further, the present invention provides various methods for detecting or monitoring the proteolytic activity of a sample.

The methods typically comprise providing a first electrode, a second electrode and an electrolytic solution comprising an electroactive species wherein a proteinaceous matrix is disposed on or in contact with at least a portion of at least the first electrode. When a potential is applied through the electrolytic solution a current is generated. When the potential is altered the current is also altered and the change in current as a function of voltage is measured at a number of time points. If the proteinaceous matrix is degraded, for example due to proteolysis the change in current as a function of voltage will be altered compared to a baseline or control measurement (typically charge versus current) where no degradation of the matrix has occurred. Typically the presence of a proteinaceous matrix severely inhibits diffusion of an electroactive species, due to the high effective viscosity. Degradation of the matrix, for example by fibrinolysis, decreases the degree of interaction between the protein fibers, thus the effective dynamic viscosity decreases leading to an increase in the apparent diffusion coefficient within the matrix or the porous support comprising the matrix, thereby allowing a change in electrochemical current.

A "baseline" is a control measurement and in some embodiments is a normal charge vs. current measurement against which a test sample can be compared. Therefore, it can be determined, based on the control or baseline charge vs. current measurement whether a sample has a measurable increase, decrease, or substantially no change in matrix degradation, as compared to the baseline level. In one aspect, the baseline level can be indicative of the proteolytic activity, in particular the fibrinolytic activity in a subject. Therefore, the term "proteolytic activity" used in reference to a baseline level of charge vs. current measurements typically refers to a baseline level established either in the absence of a sample from a subject or a population of subjects or in the presence of a sample from a subject or a population of subjects which is believed to have normal proteolytic activity and/or fibrinolytic activity. In another embodiment, the baseline can be established from a previous sample from a subject, so that the proteolytic activity of a subject can be monitored over time and/or so that the efficacy of a given therapeutic or pharmacologic agent can be evaluated over time.

The method for establishing a baseline is suitably the same method that will be used to evaluate the sample from the subject. In specific embodiments, the baseline level is established using the same sample type as the sample to be evaluated.

In certain embodiments, the baseline is established in an autologous control sample obtained from the subject. That is, the sample is obtained from the same subject from which the sample to be evaluated is obtained. The control sample is suitably the same sample type as the sample to be evaluated.

The methods may involve detecting or monitoring the proteolytic activity in a subject or a sample from the subject sample using any voltammetric method known in the art such as for example potential step voltammetry, linear sweep voltammetry or cyclic voltammetry. The proteolytic activity may be compared to a predetermined or reference charge versus current measurements to distinguish a normal subject from a subject with abnormal proteolytic activity.

The voltammetric method may be repeated with the same proteinaceous matrix with for example 30 to 60 a second waiting period between measurements. During that time a proteolytic reaction for example a plasmin fibrinolytic reaction may continue and at each time point the current response will be altered compared to previous measurements, typically the response will be more pronounced. For example, a ratio of the 30 sec or 60 sec current signal to the initial (t=0) current can be used as a measurement parameter. In this way the impact of the other parameters (active electrode surface area, $K_3Fe(CN)_6$ concentration, filter paper variability) are internally controlled for, as they do not change between the two time points. The only variable is the degree of degradation of the proteinaceous matrix such as proteolysis, e.g., fibrinolysis.

The proteinaceous matrix may be formed directly on the electrode. Alternatively, the proteinaceous matrix may be formed in solution or on a surface and at least one electrode subsequently placed in contact with the matrix. In specific embodiments, the proteinaceous matrix is formed, at least partially in a porous support and at least one electrode placed in contact with the matrix. For example, the matrix may be formed by applying a solution of protein, such as fibrinogen to the porous support and subsequently applying a polyanion, crosslinking agent or additional protein such as thrombin to the support to facilitate formation of the matrix. The porous support may then be applied to at least a portion of an electrode or the electrode inserted into the support.

In some embodiments, at least one electrode having a protein matrix disposed (e.g., by deposition) on at least a portion of its surface may be inserted into a sample putatively having proteolytic activity. FIG. 1 shows the surface of an illustrative example of an electrode of the present invention with or without a fibrin clot deposited thereon, as well as a non-limiting example of a sensor chip with multiple electrodes and synthetic matrix (filter paper) placed thereon, containing a human fibrin clot.

Figure 2:
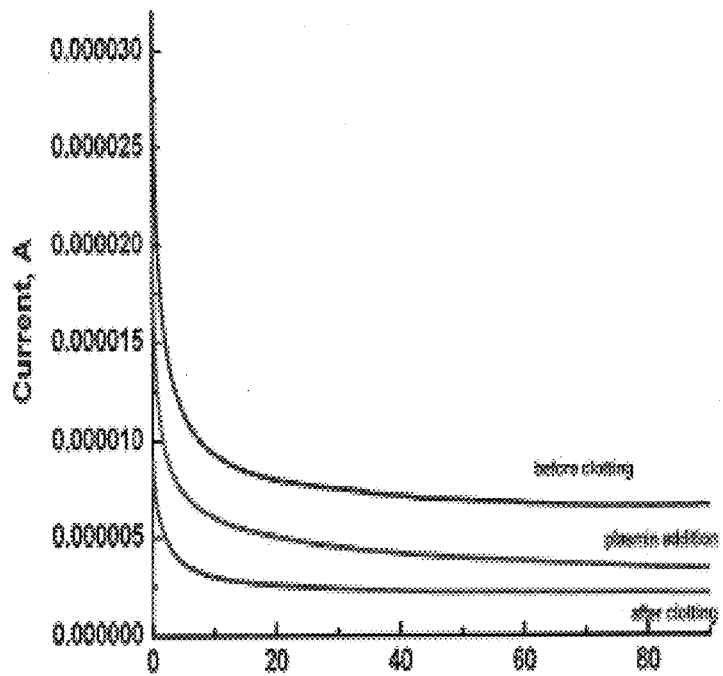
FIG. 2 shows: (A) a current versus time plot for a blank gold electrode, a gold electrode with a fibrin clot on the surface, and the gold electrode with the fibrin clot after incubation with plasmin for 7 minutes; (B) a table setting out the amperometric response of the gold electrode, the gold electrode with a fibrin clot and the gold electrode with the fibrin clot after incubation with plasmin for 7 minutes; (C) the increase in current over time after the addition (depicted by an arrow) of plasmin to a fibrin clot on a gold electrode; and (D) the increase in current over time after the addition of 87 nM plasmin to a 15 µL clot formed on a gold electrode formed with 2% fibrinogen and 1 unit thrombin.
Figure 2:
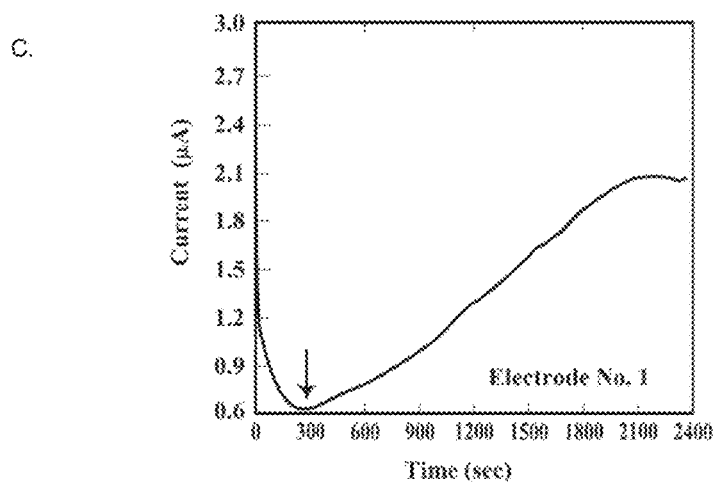
Figure 2:
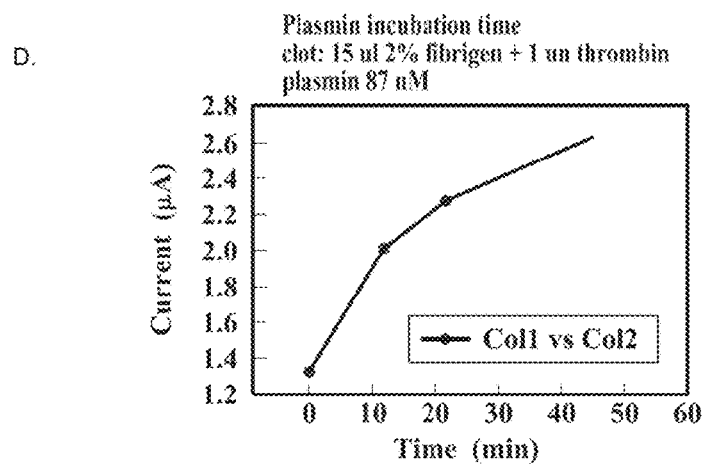

In some embodiments, the electrode is in contact with the proteinaceous matrix and a voltammetric measurement is taken, typically this is a measurement of a change in current as a function of voltage (e.g., charge versus current). Subsequent to this, a sample is applied to the porous support and further voltammetric measurements are taken wherein a difference between measurements taken before and after the application of the sample are indicative of the sample having proteolytic activity. FIG. 2 shows an illustrative example of a potential step voltammetric analysis comparing a blank gold electrode, a gold electrode with a fibrin clot on the surface, and the gold electrode with the fibrin clot after incubation with plasmin, using current at a specific time point as a measurement variable. The amperometric response of the gold electrode with the fibrin clot is markedly reduced as compared to the amperometric response of the blank gold electrode. However, after incubation with plasmin the amperometric response of the gold electrode with the fibrin clot increases.

The sample may be biological sample such as bodily fluid, excretion or secretion. For example the sample may be selected from selected from the group comprising, saliva, blood, blood plasma, blood serum, or interstitial fluid.

The sample may be obtained from a healthy subject or a subject with a disease or condition, or one that is suspected of having a disease or condition. In some embodiments, the disease or condition is associated with fibrin deposition. These diseases or conditions include deep vein thrombosis, pulmonary embolism, renal disease, hypertrophic keloid scars, coronary infarction, metastasis, inflammation, disseminated intravascular coagulation, atherosclerosis, rheumatoid arthritis, glomerulonephritis, systematic lupus erythematosus, autoimmune neuropathies, granulomatous disease, parasitic infection and allograft rejection.

In some embodiments, the disease or condition is associated with extracellular matrix degradation, an illustrative example of which includes metastatic cancer.

In some embodiments, the sample is obtained from a subject before, during or after the administration of a therapeutic agent or a treatment regimen such as those therapies or treatment regimes used in the above diseases or conditions. In such embodiments the samples are subject to voltammetric measurements as described herein as a means to detect or monitor the effect of the therapeutic agent or a treatment regimen on the ability of the subject to degrade proteinaceous matrices. For example, in embodiments where the proteinaceous matrix is a fibrin clot, the methods may be used to detect or monitor the effect of the therapeutic agent or a treatment regimen on the subject's fibrinolytic activity.

Apparatus

There is provided an apparatus for use in the detection and/or monitoring of degradation of protein matrices. The apparatus typically comprises at least electrode and a proteinaceous matrix. The matrix is typically in contact with at least a portion of the electrode. In some embodiments, the matrix may be formed directly on the electrode, for example by placing the electrode or a portion thereof in contact with a solution comprising at least one protein at least one polyanion and/or at least one crosslinking agent such that the matrix forms on the electrode. Alternatively, the matrix may be formed on the electrode by placing the electrode in contact with a solution comprising components that will form a matrix, for example a solution of fibrinogen and thrombin or a sample of blood.

Systems

Figure 3A:
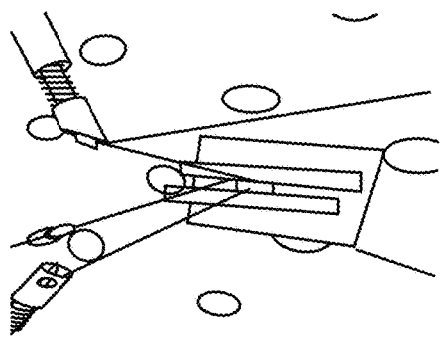
FIG. 3 shows: (A) part of a system of the invention comprising three electrodes wherein the electrodes are in contact with a fibrin clot formed in a 5×5 mm strip of Whatman grade 113 filter paper with a pore size of approximately 30 µm; (B) strips of filter paper containing human fibrin clot and impregnated with $K_3Fe(CN)_6$; (C) a filter strip impregnated with a fibrin clot and $K_3Fe(CN)_6$ and attached to a sensor chip with printed gold electrodes. Seen are the probe tips for electrical contact to a measurement instrument (potentiostat in this case) and a reference silver wire electrode.
Figure 3B:
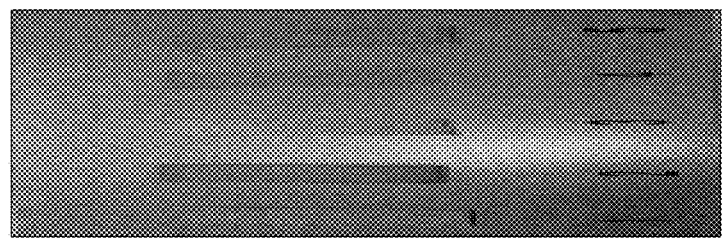

In order to perform the methods described herein, there is provided a system for performing the voltammetric detection and/or monitoring of proteolysis of a proteinaceous matrix. The system typically comprises means for voltammetric analysis including a working electrode, a counter electrode, a current measurement unit, a control unit, a data storage unit and a data processing unit. The counter electrode may include a reference electrode and an auxiliary electrode. In one aspect, the working and/or counter electrodes may be at least partially coated with a proteinaceous matrix such as a fibrin clot. Non-limiting examples of voltammetric analysis means of the present invention are shown in FIG. 3.

In specific embodiments, a working electrode is connected to a first potential supplied by a controllable variable potential source, such as those known in the art or commercially available potential sources. The current measurement unit is arranged to register the current flowing between the working electrode and the counter electrode and the current measured by the current measurement unit is used as an indicator of the proteolysis of the protein matrix. In illustrative examples, the current measurement unit comprises a current amplifier that produces an output representative of the measured current.

The control unit is typically arranged to control the second potential, the working electrode and the counter electrode and to read current values from the current measurement unit at predetermined times. In methods using cyclic voltammetry, a control cycle comprises, setting the second potential, controlling the working electrode and counter electrodes and reading current values from the current measurement unit. The control unit can comprise a memory unit in which control software is stored, or a control-interface which is controlled by an external process control system.

Figure 4:
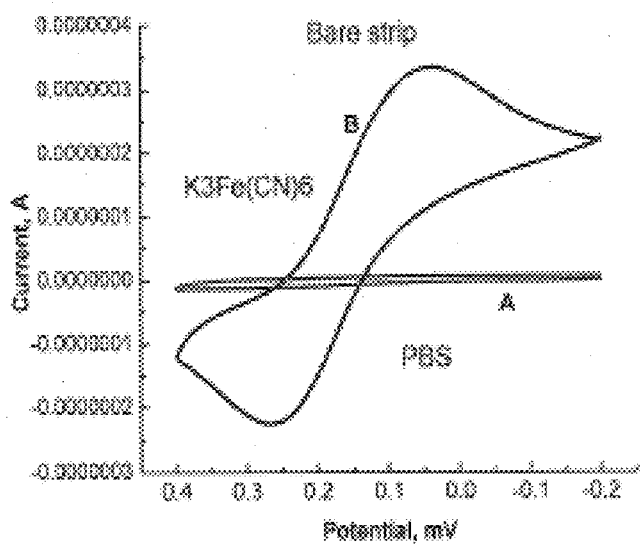
FIG. 4 shows: (A) a cyclic voltammogarm of a Whatman grade 113 filter paper strip with PBS or PBS with 10 mM ferricyanide ($Fe(CN)_6$); (B) a current versus time plot for a 0.2% fibrin clot in Whatman grade 113 filter paper in the presence of 10 mM $Fe(CN)_6$ and a current versus time plot for a 0.2% fibrin clot in Whatman grade 113 filter paper in the presence of 10 mM $Fe(CN)_6$ and plasmin; (C) a current versus time plot for a 0.2% fibrin clot in Whatman grade 113 filter paper in the presence of 10 mM $Fe(CN)_6$; (D) a current versus time plot for a 0.2% fibrin clot in Whatman grade 113 filter paper in the presence of 10 mM $Fe(CN)_6$ and plasmin.
Figure 4:
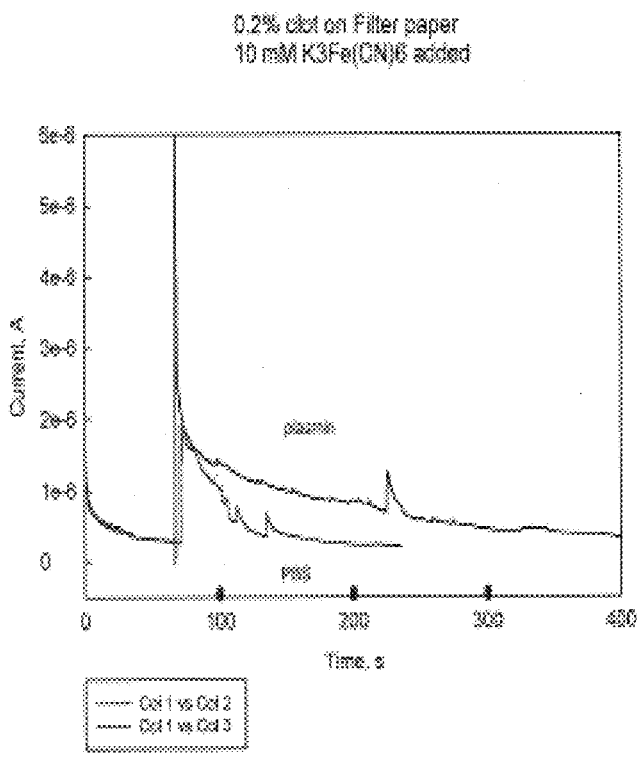
Figure 4:
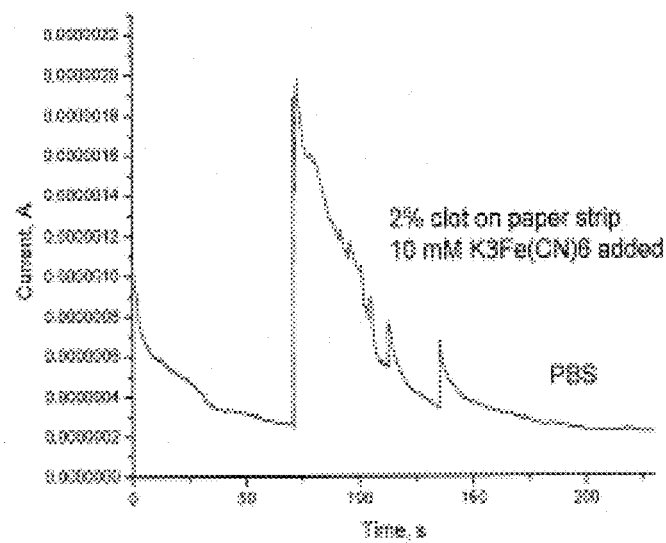
Figure 4:
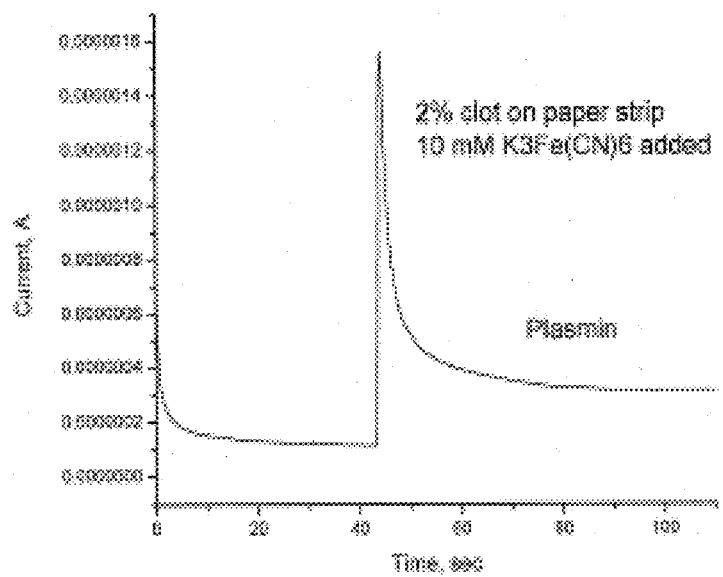
Figure 5:
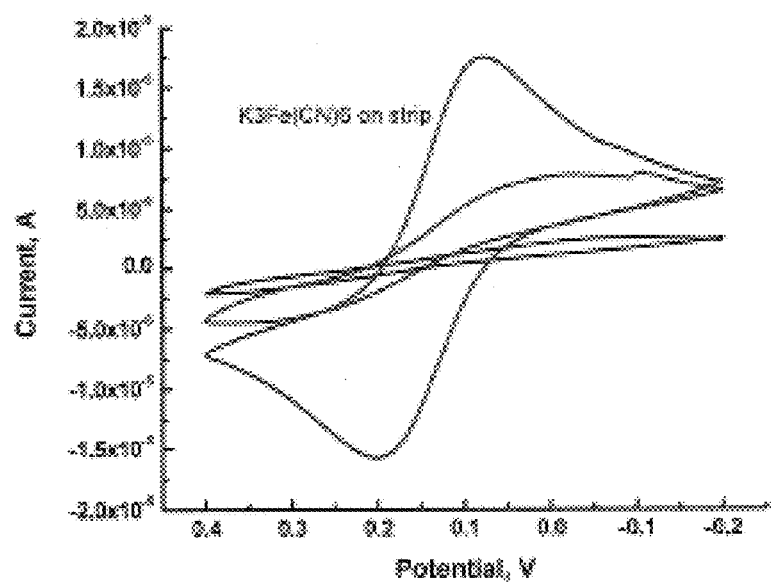
FIG. 5 shows: (A) cyclic voltammograms of a Whatman grade 113 filter paper strip with PBS or PBS with 50 mM ferricyanide ($Fe(CN)_6$); (B) a current versus time plot for a Whatman grade 113 filter paper in the presence of PBS and 50 mM $Fe(CN)_6$; (C) cyclic voltammograms of a 2.0% fibrin clot in Whatman grade 113 filter paper in the presence of PBS with 50 mM $Fe(CN)_6$ in the presence and absence of plasmin; (D) a current versus time plot for a 2.0% fibrin clot in Whatman grade 113 filter paper in the presence of PBS and 50 mM $Fe(CN)_6$ and in the presence and absence of plasmin; (E) a cyclic voltammogram of a fibrin clot in the presence (blue) and absence (red) of plasmin. (Scan rate=0.1V/sec); (F) a current vs. time (i-t) response of a fibrin clot in the presence (red) and absence (blue) of plasmin. (Potential=−50 mV); (G). a linear Scan Voltammogram of a fibrin clot in the presence (blue) and absence (red) of plasmin. (Scan rate=0.1V/sec).
Figure 5:
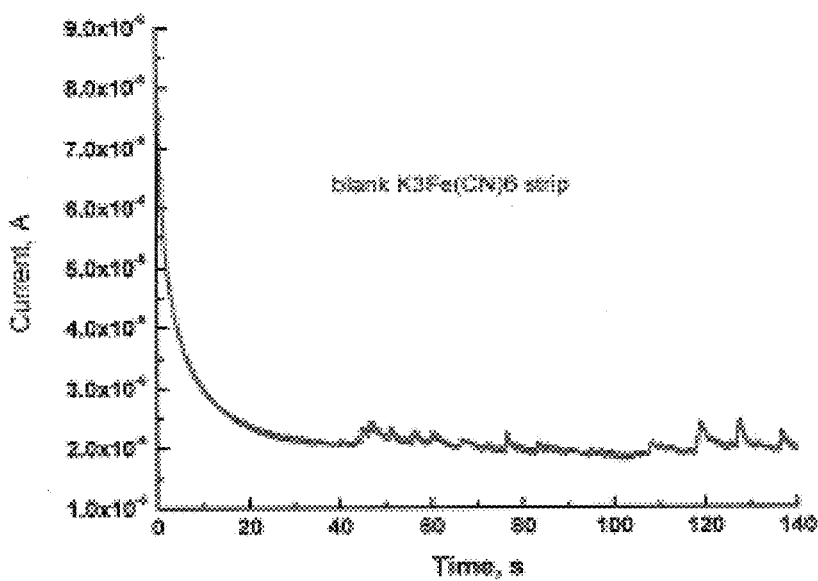
Figure 5:
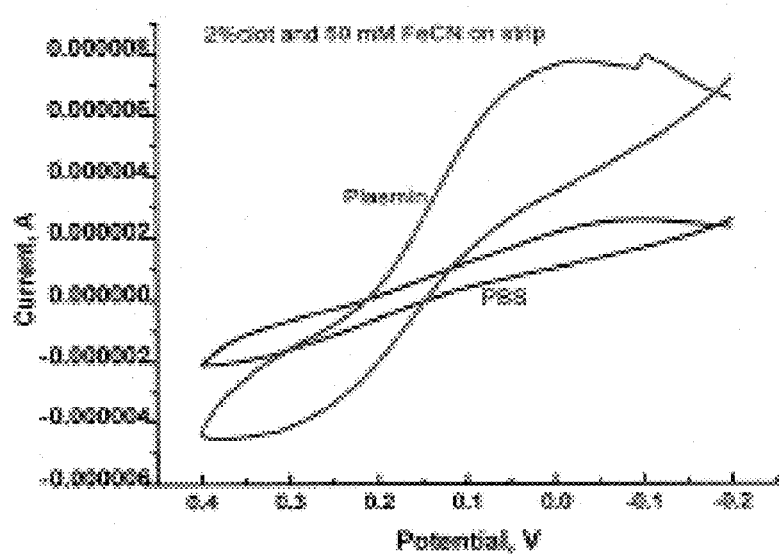
Figure 5:
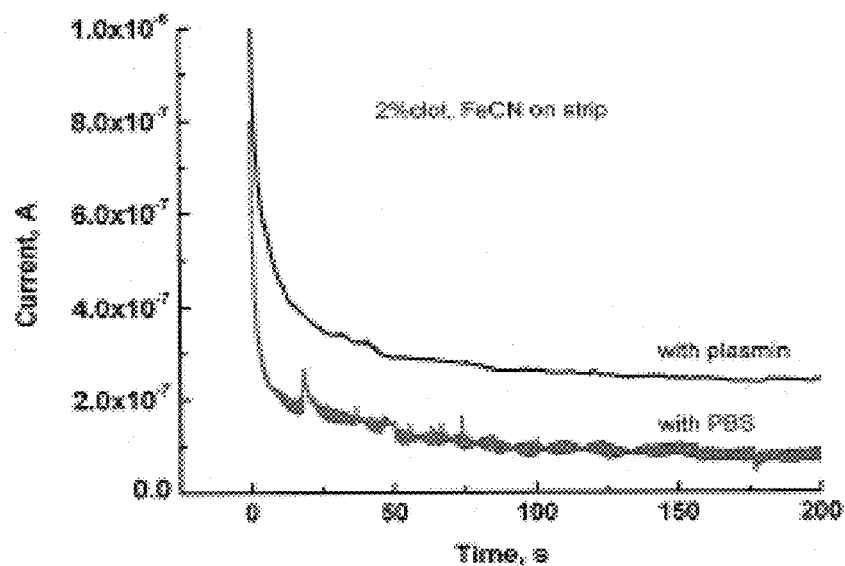
Figure 5:
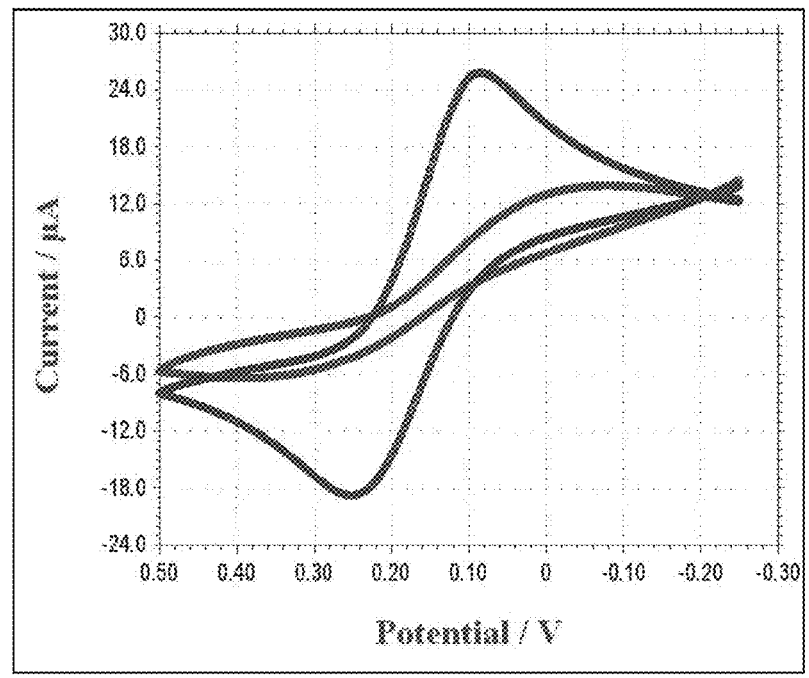
Figure 5:
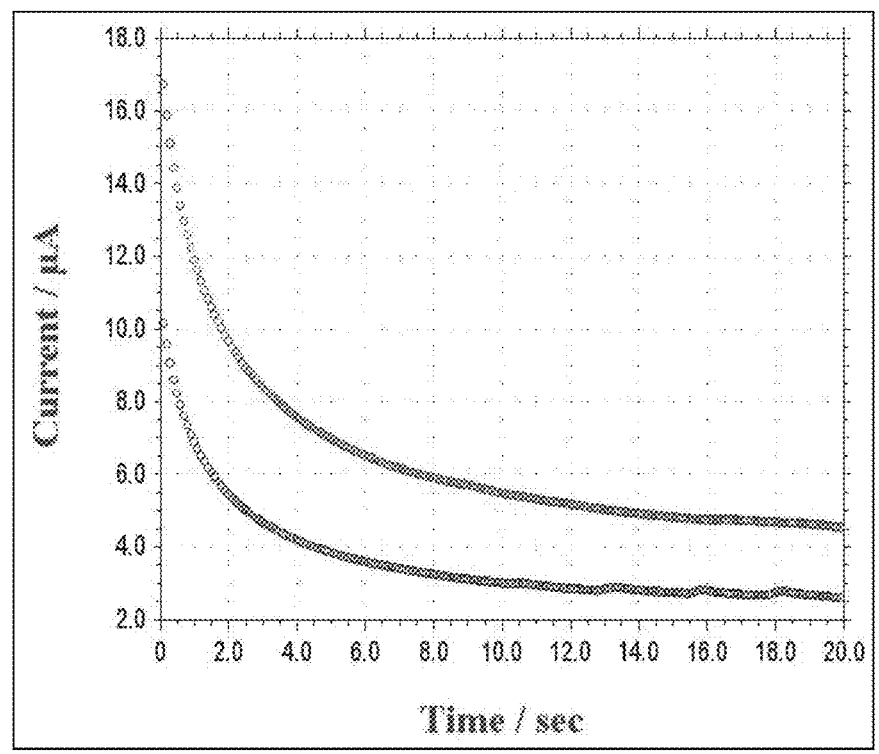
Figure 5:
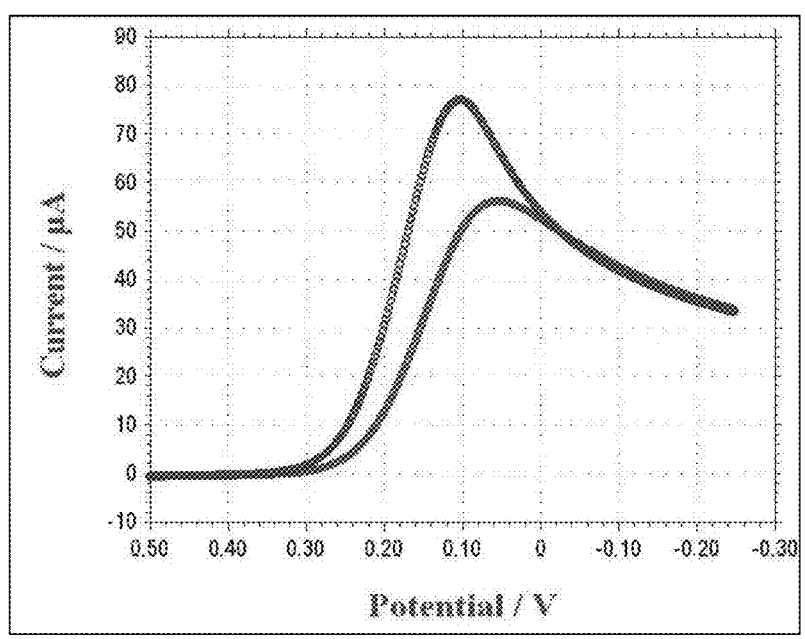

The second potential is typically supplied by a controllable variable potential source connected to the counter electrode (or the auxiliary electrode in embodiments where the counter electrode comprises a reference and auxiliary electrode), such as those known in the art or commercially available potential sources. The data storage unit stores the recorded current values, and in some embodiments comprises a commercially available memory circuit. The processing unit is used to analyze the stored current values using a predetermined mathematical model. The result of the analysis is presented, via a display or the like, such as for example the voltammograms or current versus time plots presented in FIGS. 4 and 5.

In specific embodiments, the working electrode, the counter electrode, the current measurement unit, and the control unit are integrated as a single device arranged to output the measured current values to an internal or external data storage and processing unit. The control unit may be externally controlled by an external data storage and processing unit. Accordingly, in some embodiments, an inexpensive and versatile system for detecting or monitoring proteolysis of proteinaceous matrices capable of field use or point of care use is contemplated.

In some embodiments, the systems of the invention are designed for detecting or monitoring the proteolysis of particular proteinaceous matrices such as fibrin clots. In these embodiments, the systems are desirably fully integrated, i.e., the proteinaceous matrix, the working electrode, the counter electrode, the current measurement unit, the control unit, the data storage unit and the processing unit are integrated as one device. The device may be arranged to output the result from the analysis.

Kits

The present invention also provides kits for practicing the methods disclosed herein. Typically, kits for carrying out the methods of the present invention contain all the necessary reagents to carry out those methods. In specific embodiments, a kit may comprise a support comprising a proteinaceous matrix or a support and the necessary reagent to form a protein matrix on the support such as a solution of fibrinogen and thrombin. The kit may also comprise any one or more of: (1) at least one electrode, (2) at least one electroactive species, (3) at least one electrolytic solution, (4) at least one salt and (5) at least one control sample with a known level of proteolytic activity.

The kit can also feature printed instructions for using the kit to qualitatively or quantitatively detect or monitor the proteolysis of a protein matrix in accordance with the present invention.

Fibrin Clot Embodiments

The invention also relates to a process for preparing a fibrin clot or 'mesh' for use in the methods, systems and kits of the present invention. This process generally comprises:
(a) providing a first component comprising a fibrinogen-containing material;
(b) providing a second component comprising a substance that converts fibrinogen into a fibrin clot;
(c) forming a fibrin clot-containing material by mixing the first component with the second component; and
(d) contacting the fibrin clot-containing material with at least a portion of an electrode.

The first component suitably comprises a fibrinogen-containing solution comprising at least about 2 mg/mL, at least about 5 mg/mL, or at least about 10 mg/mL fibrinogen, desirably at least about 15 mg/mL, for example from about 20 mg/mL to about 250 mg/mL or from about 20 mg/mL to about 150 mg/mL fibrinogen.

The second component suitably comprises a solution comprising thrombin. A volume of the thrombin-comprising solution is contacted with the first component to provide a final thrombin concentration/activity of less than about 1000 IU/mL, less than about 200 IU/mL, less than about 100 IU/mL, less than about 50 IU/mL, less than about 20, less than about 10 IU/mL or less than about 1 IU/mL. The thrombin can be in an active or inactive form and it is well known in the art that when thrombin is in an inactive form (e.g., a thrombin that can be activated for example by radiation or light (=photoactivatable thrombin), a larger amount of it is generally required to clot a sample of thrombin than the thrombin in an active form. The thrombin can be recombinant or synthetic or of natural origin, i.e., derived from human or animal plasma.

The fibrin clot generally has a pore diameter that substantially inhibits diffusion of an electroactive species (e.g., $K_3Fe(CN)_6$). In non-limiting examples, the pore diameter of the fibrin clot is less than about 1000 nanometers (nm), less than 100 nm, less than about 50.0 nm, less than about 20.0 nm, less than 10.0 nm, less than 5.0 nm, less than 2.0 nm, less than 1.0 nm.

The fibrin clot-containing material includes within its scope 'naked' (e.g., unsupported) fibrin clots as well as those contained or otherwise associated with a porous solid support. Acceptable supports for use in the present invention can vary widely and can be synthetic or natural, organic or inorganic, flexible or nonflexible. Representative supports include polymeric supports, such as woven and nonwoven webs (e.g., fibrous webs), microporous fibers and microporous membranes as well as particulate or beaded supports. Woven and nonwoven webs may have either regular or irregular physical configurations of surfaces.

Illustrative porous solid supports have a structure comprising pores of a diameter that is greater than the pore diameter of the fibrin clot. For example, the pore diameter is at least about 10.0 micrometers (μm), and is suitably 20 μm or more as larger pores are less restrictive to diffusion of an electroactive species. Non-limiting examples of porous supports include filter paper, sintered glass, poly(vinylidene fluoride) membrane, particulate or beaded supports such as agarose, hydrophilic polyacrylates, polystyrene, mineral oxides and Sepharose.

Suitably, the fibrin clot-containing material (e.g., naked (e.g., unsupported) or contained or otherwise associated with a porous solid support) is subjected to a mechanical or physical treatment. The mechanical treatment may include compression or extrusion. Representative physical treatments include dehydration (e.g., lyophilization, heat dehydration etc.) and radiation (e.g., light). The mechanical or physical treatment is suitably carried out under sterile conditions.

In specific embodiments, the fibrin clot-containing material comprises an electroactive species that is capable of being oxidized or reduced to form a charged species (e.g., ferricyanide, ferrocyanide, decamethylferrocene (DMFc), 1,1'-dimethylferrocene (DiMFc), 7,7,8,8-tetracyanoquinodimethane (TCNQ), ferrocene carboxylic acid, etc.).

In some embodiments, the fibrin clot-containing material is subjected to dehydration. In these embodiments, the fibrin clot-containing material is suitably rehydrated when contacted with a sample (e.g., a biological sample) under test. The dehydration can be performed in an oxygen-containing atmosphere (e.g., air), or in an inert atmosphere, such as a nitrogen atmosphere. Desirably, the dehydration is selected from lyophilization (i.e., freeze drying), heat dehydration (e.g., at ambient temperature), osmosis, filtration and centrifugation. After dehydration, the fibrin clot-containing material suitably has a low moisture content, for example a moisture content of less than about 7.5%, less than about 2%, less than about 1%, or less than about 0.5%. In specific embodiments, the fibrin clot-containing material is subjected to lyophilization so as to prepare a dry or substantially dry porous support that comprises a fibrin clot.

The fibrin clot-containing material (e.g., naked (e.g., unsupported) or contained or otherwise associated with a porous solid support) is attached to the electrode using conventional methods known to persons of skill in the art.

Fibrin clots prepared according to the above procedures or similar in vitro preparation methods—also referred to herein as 'synthetic' clots—have any one or more of the following advantages over native clots prepared from clotting native blood or plasma:

The synthetic clot can be formed in the presence of a higher level or concentration of fibrinogen (e.g., 1.5%, 2% 4%, 5%, 10%, 15% wt.), relative to native blood (0.3-0.4% wt), providing more surface for specific attachment of plasminogen/plasmin and tPA, thus allowing for faster proteolysis and faster detection The synthetic clot is not covalently crosslinked, which makes it more susceptible to proteolytic fluidization, as opposed to the rigid native clots, which are crosslinked through the action of Factor XIII.

While native clots contain covalently-linked inhibitor α-antiplasmin, to make them refractory to fibrinolysis for prolonged time under physiological conditions, the synthetic clot is prepared without α-antiplasmin, resulting in faster fibrinolysis and hence faster readout times;

The present invention will now be further described in greater detail by reference to the following specific examples, which should not be construed as in any way limiting the scope of the invention.

EXAMPLES

Example 1

Voltammetric Measurement of Proteolysis

Human fibrinogen and human thrombin stock solutions were mixed to yield 10 µL final solution (2% fibrinogen +0.1 U of thrombin final concentrations), which was vortexed and immediately applied to a 5×5 mm filter paper strip (Whatman No. 4, with large pore size, 30-40 µm particle retention). A fibrin clot was formed within the pores of the paper strip, and the strip was left to dry at room temperature for two hours. Due to the fibrinogen concentration, the clot pore-sizes were smaller than the pores in the filter paper.

Figure 3C:
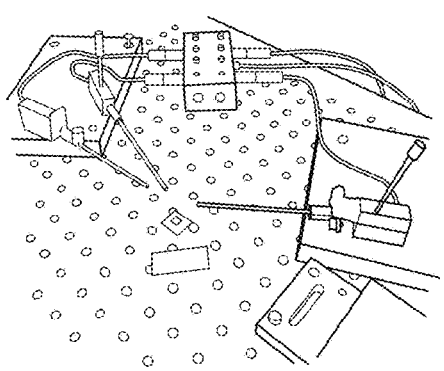

The strip-clot was impregnated with a solution of 50 mM $K_3Fe(CN)_6$, containing 0.2% Tween 20, and left to dry. The strip was attached to a chip containing flat printed electrodes (either gold or conductive carbon). An optional silver wire was attached to the strip as a reference electrode (FIG. 3C). The strip was rehydrated with a phosphate-buffered saline physiological solution (PBS), containing 2 nM human plasmin. PBS without plasmin was used as a control. Electrochemical tests were performed on the strip to determine the electrochemical current arising from reduction of $K_3Fe(CN)_6$ to $K_2Fe(CN)_6$. The current response (FIGS. 5E, F, G) was a function of several parameters: potential, electrode area, $K_3Fe(CN)_6$ concentration and diffusion coefficient.

Example 2

Collagen Matrix for Collagenase Activity

Figure 6:
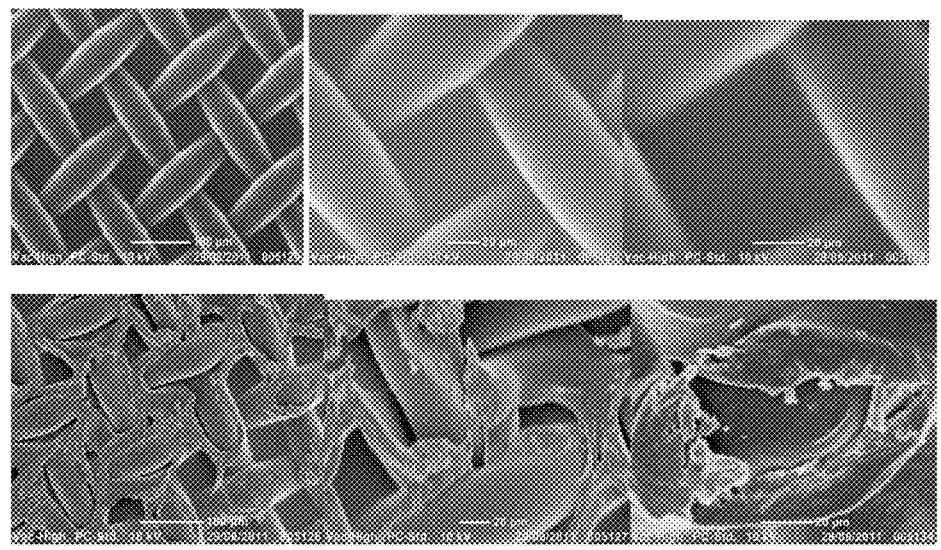
FIG. 6 shows scanning electron micrographs (SEM) of gelatin matrices on a nylon mesh membrane without (top row) and with (bottom row) protease treatment. The pore size of the intact gelatin matrix is too small to be resolved by SEM and it appears as a transparent film in the micrograph.
Figure 7:
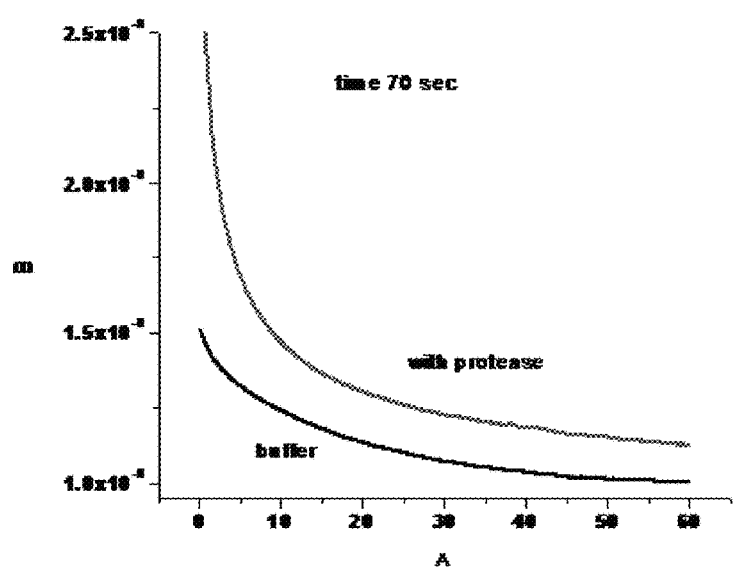
FIG. 7 shows amperometric traces on a gelatin chip with or without collagenase in the sample. X-axis shows time in seconds; Y axis shows current in Amperes.

A solution comprising 15% gelatin and 10 mM $K_3Fe(CN)_6$ was prepared, heated to 95° C. to dissolve the gelatin and deposited onto a nylon mesh membrane (70 µm pore size) by dipping the membrane into the hot solution. The gelatin membrane was let to cool-off and dry for 24 hours, before attaching it to a sensor electrode. A PBS buffer sample containing collagenase enzyme or a control PBS buffer sample with no collagenase were added to the sensor chip and the current was measured as a function of time. After the measurement, the membrane was imaged with scanning electron microscopy FIG. 6, which revealed the breakage of the gelatin matrix. FIG. 7 shows the amperometric traces in the presence or absence of collagenase.

The invention claimed is:

1. A method for detecting or monitoring proteolysis of a synthetic proteinaceous matrix comprising:
   contacting at least a portion of the synthetic proteinaceous matrix with a biological sample, wherein the synthetic proteinaceous matrix is impregnated with an electroactive species, the synthetic proteinaceous matrix is contained in or placed on a support, the synthetic proteinaceous matrix is in contact with at least a portion of a working electrode or a counter electrode, and the biological sample comprises a biological fluid;
   applying a potential to the working electrode, thereby generating an electrochemical current through the working electrode;
   measuring the electrochemical current at a plurality of times to obtain a plurality of current measurements; and
   comparing at least two of the plurality of current measurements wherein a difference between the at least two current measurements is indicative of degradation of the synthetic proteinaceous matrix in the presence of the biological sample.

2. The method of claim 1, wherein the synthetic proteinaceous matrix lacks a proteolysis inhibitor or comprises a reduced amount, level, or concentration of proteolysis inhibitor as compared to a corresponding naturally occurring proteinaceous matrix.

3. The method of claim 1, wherein the support comprises a porous support.

4. The method of claim 1, wherein the porous support has a pore diameter that substantially inhibits diffusion or mobility therethrough of the electroactive species.

5. The method of claim 1, wherein the porous support has a pore diameter that does not substantially inhibit or impede diffusion or mobility of the electroactive species.

6. The method of claim 1, wherein the support is selected from a sorbent, filter paper, sintered glass, poly(vinylidene fluoride) membrane, or gel.

7. The method of claim 1, wherein the synthetic proteinaceous matrix comprises a synthetic fibrin clot.

8. The method of claim 1, wherein the synthetic proteinaceous matrix comprises at least 1.5% fibrinogen.

9. A method for screening a sample for proteolytic activity, the method comprising;
- contacting at least a portion of a synthetic proteinaceous matrix with a biological sample, wherein the synthetic proteinaceous matrix is impregnated with an electroactive species, the synthetic proteinaceous matrix is contained in or placed on a support, the synthetic proteinaceous matrix is in contact with at least a portion of a working electrode or a counter electrode, and the biological sample comprises a biological fluid;
- applying a potential to the working electrode thereby generating an electrochemical current through the working electrode;
- measuring the current at a plurality of times; and
- comparing at least two of the measurements wherein a difference between the measurements is indicative of proteolytic activity.

10. The method of claim 9, wherein the synthetic proteinaceous matrix is a synthetic fibrin clot.

11. The method of claim 9, wherein the support is a porous support.

12. The method of claim 9, further comprising determining the amount or activity of a protease in the sample.

* * * * *